United States Patent [19]

Shiobara et al.

[11] Patent Number: 5,362,887
[45] Date of Patent: Nov. 8, 1994

[54] FLUORINE - MODIFIED ACID ANHYDRIDES

[75] Inventors: Toshio Shiobara; Koji Futatsumori; Kazuhiro Arai; Hisashi Shimizu; Shigeki Ino, all of Annaka, Japan

[73] Assignee: Shin-Etsu Chemical Co., Ltd., Tokyo, Japan

[21] Appl. No.: 216,566

[22] Filed: Mar. 23, 1994

[30] Foreign Application Priority Data

Mar. 23, 1993 [JP] Japan .................. 5-088201

[51] Int. Cl.⁵ .................. C07F 7/08; C07F 7/18
[52] U.S. Cl. .................. 549/214; 549/215
[58] Field of Search .................. 549/214, 215

[56] References Cited

U.S. PATENT DOCUMENTS

| | | | |
|---|---|---|---|
| 4,176,124 | 11/1979 | Darms et al. | 549/214 |
| 4,261,898 | 4/1981 | Darms et al. | 549/214 |
| 4,837,339 | 6/1989 | Sato | 549/214 |
| 5,117,001 | 5/1992 | Okinoshima et al. | 549/214 |

*Primary Examiner*—Paul F. Shaver
*Attorney, Agent, or Firm*—Millen, White, Zelano & Branigan

[57] ABSTRACT

Novel fluorine-modified acid anhydrides of formula (1) are useful curing agents typically in epoxy resin compositions for encapsulating semiconductor devices.

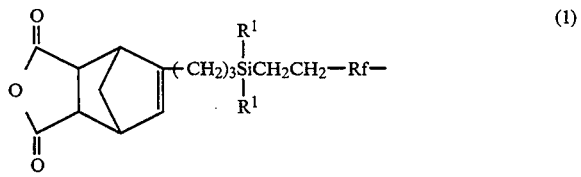

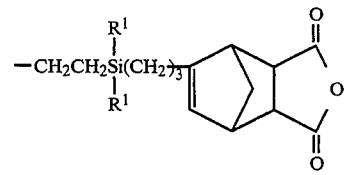

$R^1$ is a hydrogen atom, substituted or unsubstituted monovalent hydrocarbon group, hydroxyl group, alkoxy group or alkenyloxy group. Rf is a divalent perfluoroalkylene or perfluoropolyether group of the general formula (2):

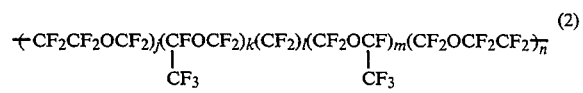

wherein $l$ is an integer of 0 to 8, $k$ and $m$ are integers of 0 to 15, $j$ and $n$ are 0 or 1, with the proviso that $j$, $k$, $l$, $m$ and $n$ are not equal to 0 at the same time.

4 Claims, No Drawings

FLUORINE - MODIFIED ACID ANHYDRIDES

BACKGROUND OF THE INVENTION

1. Field of the Invention

This invention relates to novel fluorine-modified acid anhydrides suitable for use in the manufacture of epoxy resin compositions for encapsulating semiconductor devices.

2. Prior Art

Heretofore, epoxy resins have been widely utilized in various molding materials, powder coating materials, electrically insulating materials, and other engineering materials by blending them with curing agents and inorganic fillers to form epoxy resin compositions. Currently, epoxy resins find a great demand as semiconductor device encapsulating compositions since they are generally excellent in molding, adhesion, electrical properties, mechanical properties, and moisture resistance as compared with other conventional thermosetting resins.

Recently, the semiconductor device encapsulation technique is on a transition from the conventional transfer molding technique to a new encapsulation technique using liquid epoxy resin compositions. In such compositions, acid anhydrides are often used as a curing agent.

Conventional acid anhydrides used as a curing agent for liquid or transparent epoxy resins, however, are generally hygroscopic and less flexible, leaving some problems. For example, in a solder crack test of dipping encapsulated semiconductor device packages in solder after moisture absorption, cracks often occur in the packages. Also during the step of encapsulating semiconductor elements and during a thermal cycling test on encapsulated semiconductor devices, package cracks occur or excess stresses are exerted to deform the elements, causing a function lowering or failure.

Regarding these problems, the same assignee as the present invention previously proposed an epoxy resin composition having an organopolysiloxane blended in a curable epoxy resin in Japanese Patent Application Kokai (JP-A) No. 129246/1981 and an epoxy resin composition having a block copolymer of an aromatic polymer and an organopolysiloxane added to a curable epoxy resin in JP-A 21417/1983. These epoxy resin compositions were improved in crack resistance.

Nevertheless, increasingly strict requirements are now imposed on semiconductor device encapsulating materials. There is a desire to have an epoxy resin composition which is further improved in crack resistance. Especially for liquid or transparent epoxy resins, it is desired to use acid anhydrides which are more water repellent and flexible as a curing agent.

SUMMARY OF THE INVENTION

Therefore, an object of the present invention is to provide a novel and improved fluorine-modified acid anhydride which is suitable for use in coating compositions, adhesives, and polyimide resin compositions as well as epoxy resin compositions for encapsulating semiconductor devices.

We have found that a novel fluorine-modified acid anhydride of the following formula (1) is obtained by subjecting an alkenyl group-containing acid anhydride of the following formula (4) to addition reaction with a specific fluorine compound having a silylidyne ($\equiv$SiH) group, that is, a fluorinated organic silicon compound of the following formula (3) according to the following reaction scheme.

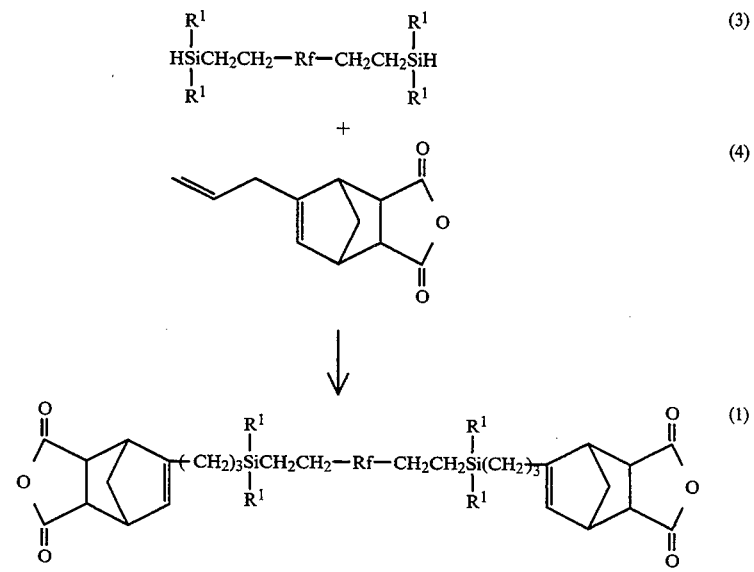

In the formulae, $R^1$ is selected from the group consisting of a hydrogen atom, substituted or unsubstituted monovalent hydrocarbon group, hydroxyl group, alkoxy group, and alkenyloxy group, and Rf is a divalent perfluoroalkylene or perfluoropolyether group of the general formula (2):

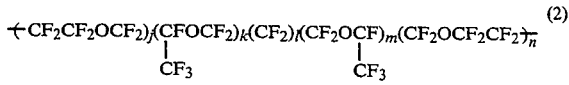

wherein l is an integer of 0 to 8, k and m are integers of 0 to 15, j and n are 0 or 1, with the proviso that j, k, l, m and n are not equal to 0 at the same time.

The fluorine-modified acid anhydride of the invention is prepared through addition reaction wherein a silylidyne group of the fluorinated organic silicon compound of formula (3) adds to an alkenyl group of the acid anhydride of formula (4). By this addition reaction, there is readily obtained a fluorine-modified acid anhydride which is substantially devoid of a free fluorinated organic silicon compound not bound to the acid anhydride. A mixture or one of the thus obtained fluorine-modified acid anhydrides is blended with a conventional well-known epoxy resin together with a conventional well-known curing agent, especially acid anhydride curing agent, to form an epoxy resin composition which cures to a low stressed, water repellent, tough cured product. That is, this epoxy resin composition can be molded and cured into a product having improved crack resistance without lowering the glass transition temperature. Therefore, the fluorine-modified acid anhydride of the invention is a very useful curing agent for a semiconductor device encapsulating epoxy resin composition. Particularly when used in an epoxy resin composition required to be transparent, the fluorine-modified acid anhydride of the invention is effective in all these properties without detracting from transparency.

DETAILED DESCRIPTION OF THE INVENTION

The present invention provides fluorine-modified acid anhydrides of the general formula (1) which are novel.

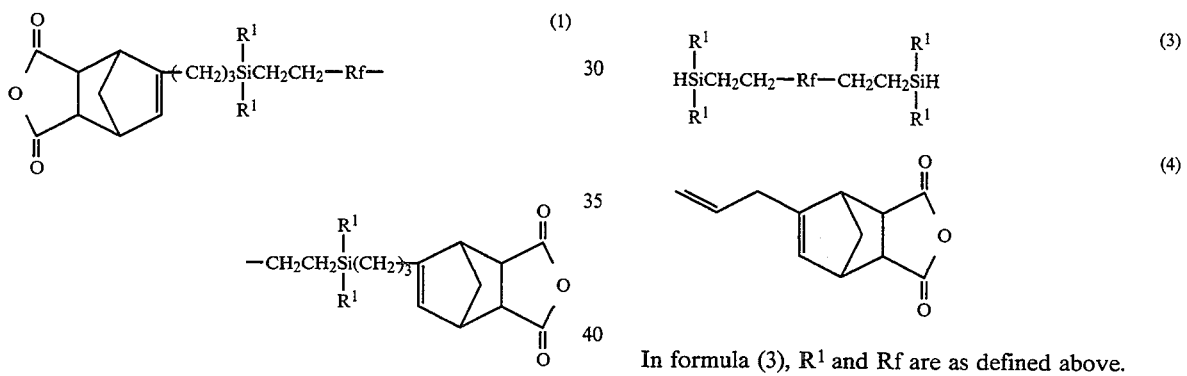

In the formula, $R^1$ is a hydrogen atom, a substituted or unsubstituted monovalent hydrocarbon group preferably having 1 to 6 carbon atoms, a hydroxyl group, an alkoxy group preferably having 1 to 6 carbon atoms or an alkenyloxy group preferably having 2 to 6 carbon atoms.

Rf is a divalent perfluoroalkylene or perfluoropolyether group of the general formula (2):

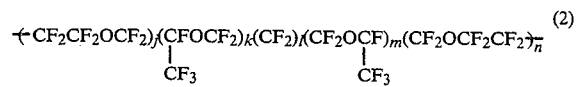

wherein l is an integer of 0 to 8, k and m are integers of 0 to 15, j and n are 0 or 1, with the proviso that j, k, l, m and n are not equal to 0 at the same time.

Examples of the unsubstituted monovalent hydrocarbon group include methyl, ethyl, phenyl and benzyl groups. Examples of the substituted monovalent hydrocarbon group include chloropropyl, chloromethyl, and glycidylpropyl groups. Exemplary alkoxy groups are methoxy and ethoxy groups, and exemplary alkenyloxy groups are isopropenyloxy and isobutenyloxy groups.

The fluorine-modified acid anhydride of formula (1) is obtained by effecting addition reaction between a fluorinated organic silicon compound of the following general formula (3) and an alkenyl group-containing acid anhydride of the following general formula (4).

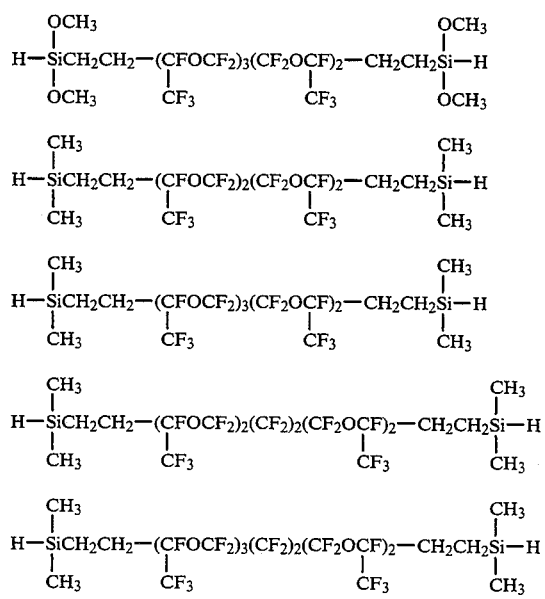

In formula (3), $R^1$ and Rf are as defined above.

Several illustrative, non-limiting examples of the fluorine-modified acid anhydride are given below.

$$H-\underset{\underset{OCH_3}{|}}{\overset{\overset{OCH_3}{|}}{Si}}CH_2CH_2-(CFOCF_2)_3(CF_2OCF)_2-CH_2CH_2\underset{\underset{OCH_3}{|}}{\overset{\overset{OCH_3}{|}}{Si}}-H$$
$$\qquad\qquad\qquad\qquad CF_3 \qquad\quad CF_3$$

$$H-\underset{\underset{CH_3}{|}}{\overset{\overset{CH_3}{|}}{Si}}CH_2CH_2-(CFOCF_2)_2(CF_2OCF)_2-CH_2CH_2\underset{\underset{CH_3}{|}}{\overset{\overset{CH_3}{|}}{Si}}-H$$
$$\qquad\qquad\qquad\qquad CF_3 \qquad\quad CF_3$$

$$H-\underset{\underset{CH_3}{|}}{\overset{\overset{CH_3}{|}}{Si}}CH_2CH_2-(CFOCF_2)_3(CF_2OCF)_2-CH_2CH_2\underset{\underset{CH_3}{|}}{\overset{\overset{CH_3}{|}}{Si}}-H$$
$$\qquad\qquad\qquad\qquad CF_3 \qquad\quad CF_3$$

$$H-\underset{\underset{CH_3}{|}}{\overset{\overset{CH_3}{|}}{Si}}CH_2CH_2-(CFOCF_2)_2(CF_2)_2(CF_2OCF)_2-CH_2CH_2\underset{\underset{CH_3}{|}}{\overset{\overset{CH_3}{|}}{Si}}-H$$
$$\qquad\qquad\qquad\qquad CF_3 \qquad\qquad\quad CF_3$$

$$H-\underset{\underset{CH_3}{|}}{\overset{\overset{CH_3}{|}}{Si}}CH_2CH_2-(CFOCF_2)_3(CF_2)_2(CF_2OCF)_2-CH_2CH_2\underset{\underset{CH_3}{|}}{\overset{\overset{CH_3}{|}}{Si}}-H$$
$$\qquad\qquad\qquad\qquad CF_3 \qquad\qquad\quad CF_3$$

-continued

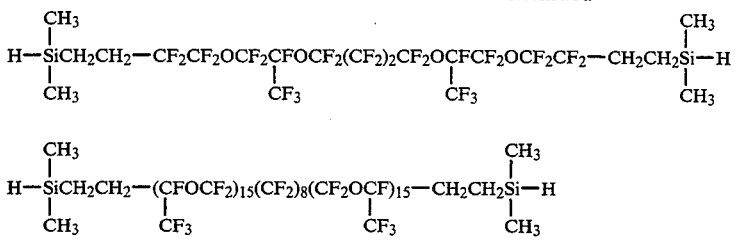

15

The method for preparing a fluorine-modified acid anhydride according to the present invention involves the step of effecting addition reaction between the fluorine-containing organic silicon compound and the alkenyl group-containing acid anhydride both defined above. For promoting the addition reaction, any of conventional well-known catalysts, typically a platinum series catalyst such as chloroplatinic acid may be used. Reaction is preferably effected in a solvent, for example, an inert solvent such as meta-xylene hexafluoride and a mixture of methyl isobutyl ketone and an inert solvent such as meta-xylene hexafluoride. The reaction temperature, which is not critical, preferably ranges from about 60° C. to about 160° C. and the reaction time is generally from about ½ to about 10 hours.

In the practice of the invention, the fluorinated organic silicon compound of formula (3) and the alkenyl group-containing acid anhydride of formula (4) are preferably used in such amounts to meet $0.1 \leq B/A \leq 2$, especially $0.8 \leq B/A \leq 1.2$ wherein A is the equivalent of alkenyl group in the acid anhydride and B is the equivalent of ≡SiH group in the fluorinated organic silicon compound. With $B/A < 0.1$, more alkenyl group-containing acid anhydride is left unreacted and its removal at the end of reaction would sometimes require undesired steps. With $B/A > 2$, it would sometimes be difficult to remove the unreacted fluorinated organic silicon compound.

The fluorine-modified acid anhydrides of the present invention, either alone or in admixture of two or more, are effective for curing conventional well-known epoxy resins, optionally in the presence of curing catalysts such as organic tin compounds. Such epoxy resin compositions cure to tough cured products which are of low stress, water repellent, and crack resistant, without lowering the glass transition temperature.

Therefore, the fluorine-modified acid anhydride of the invention is advantageously used in epoxy resin compositions as a curing agent or stress lowering agent. When used as an acid anhydride component in preparing a polyimide resin, the fluorine-modified acid anhydride is effective in providing the polyimide with high water repellency and low modulus of elasticity.

It will be understood that when the fluorine-modified acid anhydrides of the invention are used alone or in admixture as a curing agent for epoxy resin, the remaining components may be those commonly used in conventional epoxy resin compositions. For example, one or a mixture of the fluorine-modified acid anhydrides of the invention is used singly or in admixture with a conventional acid anhydride and blended with an epoxy resin together with a curing accelerator, filler, flame retardant, coupling agent and other additives to form an epoxy resin composition which is useful as a coating composition, adhesive, semiconductor encapsulant, semiconductor surface protective film or the like.

The fluorine-modified acid anhydrides of the invention are advantageously used in semiconductor encapsulating materials. The method of the invention is a simple efficient process for producing the fluorine-modified acid anhydride.

EXAMPLE

The examples of the present invention are given below by way of illustration and not by way of limitation.

EXAMPLE 1

The reactor used was a four-necked flask of 3 liters in interior volume equipped with a reflux condenser, thermometer, stirrer, and dropping funnel. The flask was charged with 108 grams of an acid anhydride of formula (I) shown below and 320 grams of meta-xylene hexafluoride as a solvent. After azeotroping off water, 6.5 grams of a chloroplatinic acid catalyst (PL-50T manufactured by Shin-Etsu Chemical Co., Ltd.) was added. With stirring, 166.7 grams of a fluorine compound of average compositional formula (II) shown below was added dropwise over 30 minutes to the flask at a temperature of 130° C. stirring was continued for a further 9 hours at the temperature. From the thus obtained reaction product, the unreacted acid anhydride and solvent were distilled off under vacuum, yielding 230 grams of the end fluorine-modified acid anhydride. This acid anhydride appeared as a pale yellow transparent liquid.

IR analysis of the fluorine-modified acid anhydride showed the disappearance of the absorption band at 2130 cm¹ indicative of the presence of a ≡SiH group. NMR analysis showed the disappearance of the peak near 4.0 ppm indicative of the presence of a ≡SiH group. Gas permeation chromatography (GPC) analysis showed the appearance of a peak indicative of the presence of a compound having a higher molecular weight than the starting reactant. By these analytical data, coupled with the results of elemental analysis, the fluorine-modified acid anhydride was identified to have the following structural formula (III).

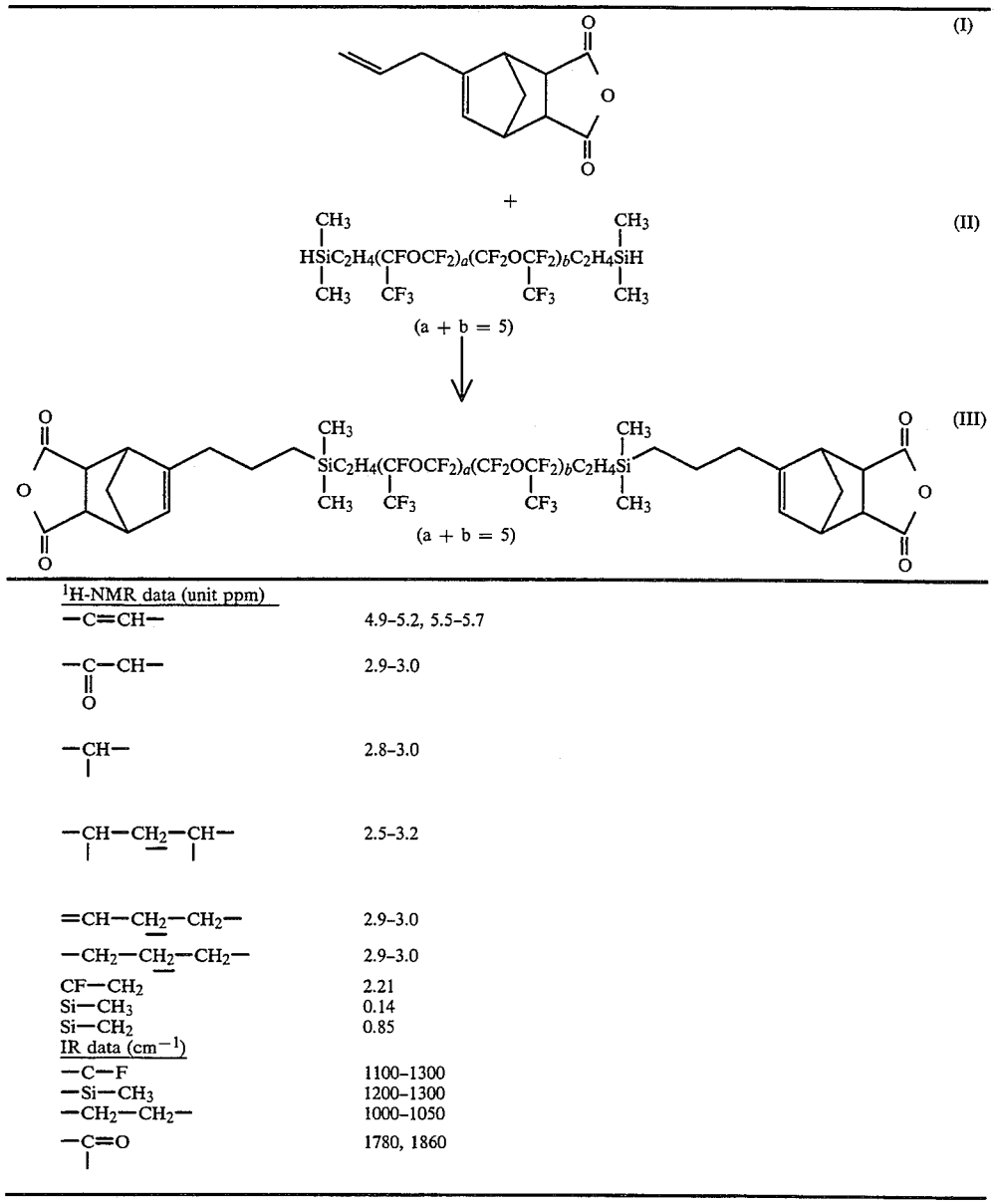

| $^1$H-NMR data (unit ppm) | |
|---|---|
| —C=CH— | 4.9–5.2, 5.5–5.7 |
| —C(=O)—CH— | 2.9–3.0 |
| —CH— | 2.8–3.0 |
| —CH—CH$_2$—CH— | 2.5–3.2 |
| =CH—CH$_2$—CH$_2$— | 2.9–3.0 |
| —CH$_2$—CH$_2$—CH$_2$— | 2.9–3.0 |
| CF—CH$_2$ | 2.21 |
| Si—CH$_3$ | 0.14 |
| Si—CH$_2$ | 0.85 |
| IR data (cm$^{-1}$) | |
| —C—F | 1100–1300 |
| —Si—CH$_3$ | 1200–1300 |
| —CH$_2$—CH$_2$— | 1000–1050 |
| —C=O | 1780, 1860 |

Elemental analysis data (wt %), theoretical values from the structural formula are in parentheses

| | |
|---|---|
| F | 40.6 (40.4) |
| C | 39.7 (39.9) |
| O | 12.6 (12.5) |
| H | 3.30 (3.26) |
| Si | 3.80 (3.94) |

EXAMPLE 2

The reactor was a four-necked flask as used in Example 1. The flask was charged with 108 grams of an acid anhydride of formula (I) shown below and 320 grams of metaxylene hexafluoride as a solvent. After azeotroping off water, 6.5 grams of a chloroplatinic acid catalyst (PL-50T manufactured by Shin-Etsu Chemical Co., Ltd.) was added. With stirring, 89.3 grams of a fluorine compound of average compositional formula (IV) shown below was added dropwise over 30 minutes to the flask at a temperature of 130° C. Stirring was continued for a further 10 hours at the temperature. From the thus obtained reaction product, the unreacted acid anhydride and solvent were distilled off under vacuum, yielding 160 grams of the end fluorine-modified acid anhydride. This acid anhydride appeared as a pale yellow transparent liquid.

IR analysis of the fluorine-modified acid anhydride showed the disappearance of the absorption band at 2130 cm$^1$ indicative of the presence of a ≡SiH group. NMR analysis showed the disappearance of the peak near 4.0 ppm indicative of the presence of a ≡SiH group. GPC analysis showed the appearance of a peak indicative of the presence of a compound having a higher molecular weight than the starting reactant. By these analytical data, coupled with the results of elemental analysis, the fluorine-modified acid anhydride was identified to have the following structural formula (V).

compound of average compositional formula (VI) shown below was added dropwise over 30 minutes to

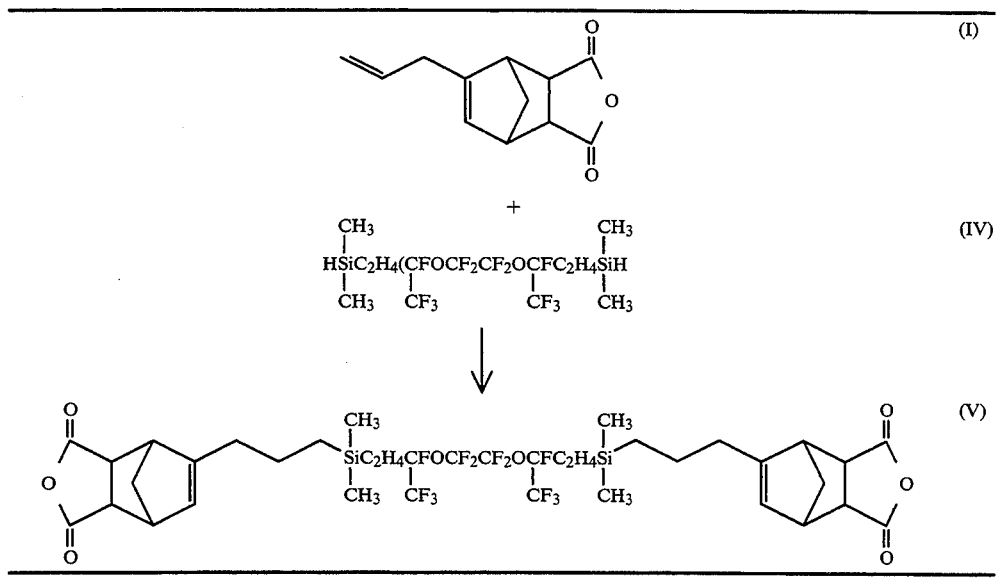

| $^1$H-NMR data (unit ppm) | |
|---|---|
| —C=CH— | 4.9–5.2, 5.5–5.7 |
| —C—CH—<br>‖<br>O | 2.9–3.0 |
| —CH—<br>\| | 2.8–3.1 |
| —CH—CH$_2$—CH—<br>\|         \| | 2.5–3.2 |
| =CH—CH$_2$—CH$_2$— | 2.9–3.0 |
| —CH$_2$—CH$_2$—CH$_2$— | 2.9–3.0 |
| CF—CH$_2$ | 2.21 |
| Si—CH$_3$ | 0.14 |
| Si—CH$_2$ | 0.85 |
| IR data (cm$^{-1}$) | |
| —C—F | 1100–1300 |
| —Si—CH$_3$ | 1200–1300 |
| —CH$_2$—CH$_2$— | 1000–1050 |
| —C=O<br>\| | 1780, 1860 |

Elemental analysis data (wt %), theoretical values from the structural formula are in parentheses

| | |
|---|---|
| F | 25.2 (25.0) |
| C | 49.7 (49.9) |
| O | 14.1 (14.0) |
| H | 5.1 (5.0) |
| Si | 5.9 (6.1) |

EXAMPLE 3

The reactor was a four-necked flask as used in Example 1. The flask was charged with 108 grams of an acid anhydride of formula (I) shown below and 210 grams of meta-xylene hexafluoride as a solvent. After azeotroping off water, 6.5 grams of a chloroplatinic acid catalyst (PL-50T manufactured by Shin-Etsu Chemical Co., Ltd.) was added. With stirring, 980.1 grams of a fluorine compound of average compositional formula (VI) shown below was added dropwise over 30 minutes to the flask at a temperature of 130° C. Stirring was continued for a further 5 hours at the temperature. From the thus obtained reaction product, the unreacted acid anhydride and solvent were distilled off under vacuum, yielding 1042 grams of the end fluorine-modified acid anhydride. This acid anhydride appeared as a pale yellow transparent liquid.

IR analysis of the fluorine-modified acid anhydride showed the disappearance of the absorption band at 2130 cm$^1$ indicative of the presence of a ≡SiH group. NMR analysis showed the disappearance of the peak near 4.0 ppm indicative of the presence of a ≡SiH group. GPC analysis showed the appearance of a peak indicative of the presence of a compound having a higher molecular weight than the starting reactant. By these analytical data, coupled with the results of elemental analysis, the fluorine-modified acid anhydride was identified to have the following structural formula (VII).

compound of average compositional formula (VIII) shown below was added dropwise over 30 minutes to

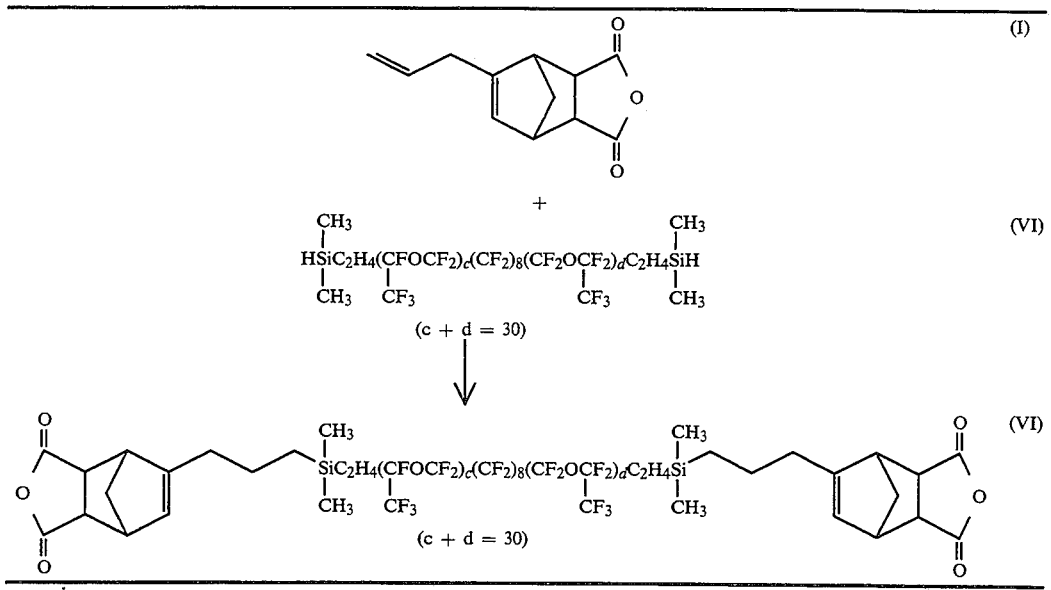

| $^1$H-NMR data (unit ppm) | |
|---|---|
| —C=CH— | 4.9–5.2, 5.5–5.7 |
| —C—CH—<br>‖<br>O | 2.9–3.0 |
| —CH—<br>\| | 2.8–3.1 |
| —CH—CH$_2$—CH—<br>\|  —  \| | 2.5–3.2 |
| =CH—CH$_2$—CH$_2$— | 2.9–3.0 |
| —CH$_2$—CH$_2$—CH$_2$— | 2.9–3.0 |
| CF—CH$_2$ | 2.21 |
| Si—CH$_3$ | 0.14 |
| Si—CH$_2$ | 0.85 |
| IR data (cm$^{-1}$) | |
| —C—F | 1100–1300 |
| —Si—CH$_3$ | 1200–1300 |
| —CH$_2$—CH$_2$— | 1000–1050 |
| —C=O<br>\| | 1780, 1860 |

Elemental analysis data (wt %), theoretical values from the structural formula are in parentheses

| F | 62.6 (62.4) |
|---|---|
| C | 26.0 (26.2) |
| O | 9.5 (9.70) |
| H | 0.90 (0.77) |
| Si | 1.0 (0.93) |

EXAMPLE 4

The reactor was a four-necked flask as used in Example 1. The flask was charged with 108 grams of an acid anhydride of formula (I) shown below and 320 grams of meta-xylene hexafluoride as a solvent. After azeotroping off water, 6.5 grams of a chloroplatinic acid catalyst (PL-50T manufactured by Shin-Etsu Chemical Co., Ltd.) was added. With stirring, 170.5 grams of a fluorine the flask at a temperature of 130° C. Stirring was continued for a further 9 hours at the temperature. From the thus obtained reaction product, the unreacted acid anhydride and solvent were distilled off under vacuum, yielding 230 grams of the end fluorine-modified acid anhydride. This acid anhydride appeared as a pale yellow transparent liquid.

IR analysis of the fluorine-modified acid anhydride showed the disappearance of the absorption band at 2130 cm$^1$ indicative of the presence of a ≡SiH group. NMR analysis showed the disappearance of the peak near 4.0 ppm indicative of the presence of a ≡SiH group. GPC analysis showed the appearance of a peak indicative of the presence of a compound having a higher molecular weight than the starting reactant. By these analytical data, coupled with the results of elemental analysis, the fluorine-modified acid anhydride was identified to have the following structural formula (IX).

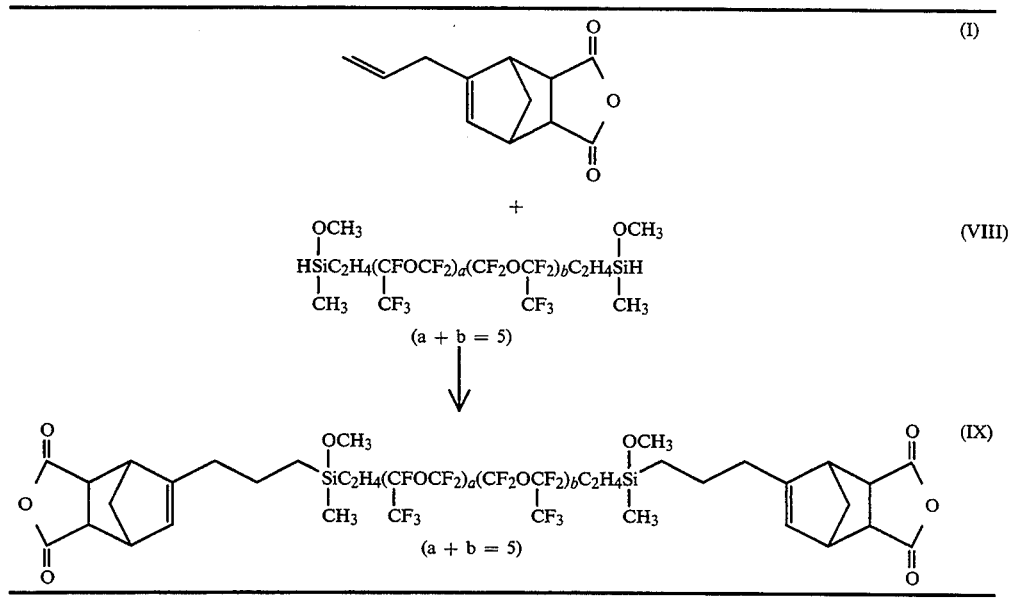

| $^1$H-NMR data (unit ppm) | |
|---|---|
| —C=CH— | 4.9–5.2, 5.5–5.7 |
| —C(=O)—CH— | 2.9–3.0 |
| —CH— | 2.8–3.1 |
| —CH—CH$_2$—CH— | 2.5–3.2 |
| =CH—CH$_2$—CH$_2$— | 2.9–3.0 |
| —CH$_2$—CH$_2$—CH$_2$— | 2.9–3.0 |
| CF—CH$_2$ | 2.21 |
| Si—CH$_3$ | 0.14 |
| Si—CH$_2$ | 0.85 |
| IR data (cm$^{-1}$) | |
| —C—F | 1100–1300 |
| —Si—CH$_3$ | 1200–1300 |
| —CH$_2$—CH$_2$— | 1000–1050 |
| —C=O | 1780, 1860 |

Elemental analysis data (wt %), theoretical values from the structural formula are in parentheses

| F | 41.0 (41.1) |
|---|---|
| C | 37.0 (37.2) |
| O | 14.8 (15.0) |
| H | 2.9 (2.7) |
| Si | 4.3 (4.0) |

We claim:
1. A fluorine-modified acid anhydride of the formula (1):

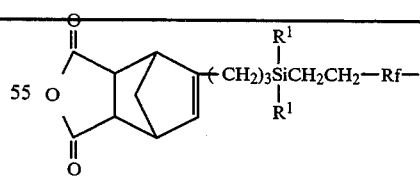

(1)

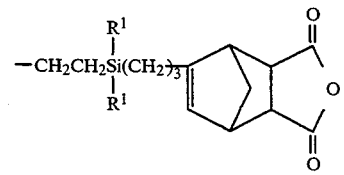

wherein R$^1$ is selected from the group consisting of a hydrogen atom, substituted or unsubstituted monovalent hydrocarbon group, hydroxyl group, alkoxy group, and alkenyloxy group, and Rf is a divalent perfluoroalkylene or perfluoropolyether group of the formula (2):

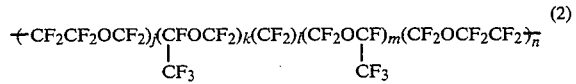

wherein l is an integer of 0 to 8, k and m are integers of 0 to 15, j and n are 0 or 1, with the proviso that j, k, l, m and n are not equal to 0 at the same time.

2. The fluorine-modified acid anhydride of claim 1 wherein $R^1$ is selected from the group consisting of a hydrogen atom, methyl group, ethyl group, phenyl group, benzyl group, chloropropyl group, chloromethyl group, glycidylpropyl group, methoxy group, ethoxy group, isopropenyloxy group, isobutenyloxy group, and hydroxyl group.

3. The fluorine-modified acid anhydride of claim 1, selected from the group consisting of the following formulae:

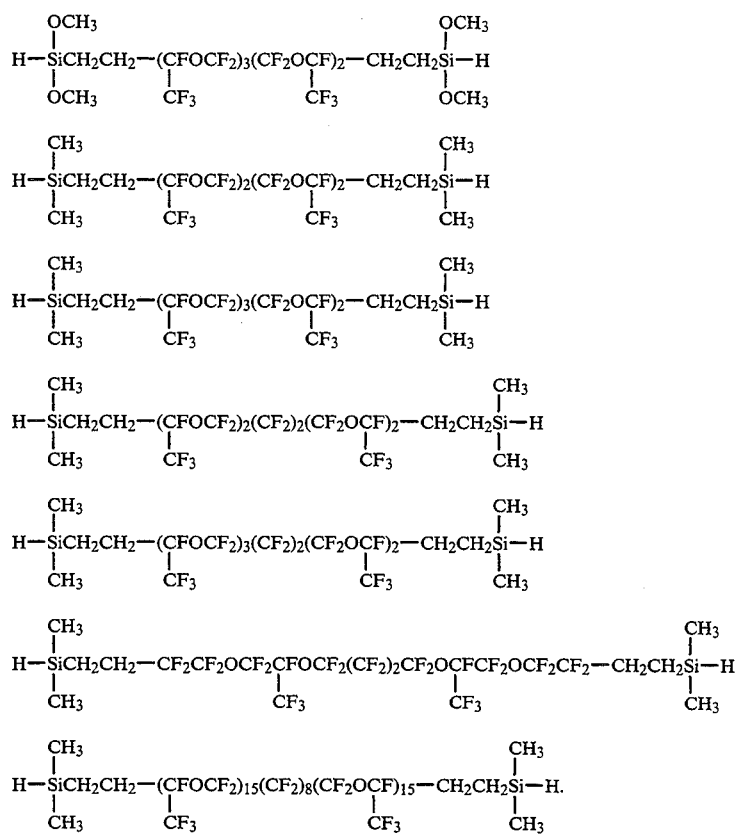

4. The fluorine-modified acid anhydride of claim 1, wherein $R^1$ is selected from the group consisting of a hydrogen atom, a substituted or unsubstituted monovalent hydrocarbon group of 1 to 6 carbon atoms, a hydroxyl group, an alkoxy group having 1 to 6 carbon atoms and an alkenyloxy group having 2 to 6 carbon atoms.

* * * * *